United States Patent
Petruson

(10) Patent No.: US 9,138,406 B2
(45) Date of Patent: Sep. 22, 2015

(54) COMPOSITION FOR COMBATING EPISTAXIS

(75) Inventor: Björn Petruson, Göteborg (SE)

(73) Assignee: PHARMACURE HEALTH CARE AB, Göteborg (SE)

( * ) Notice: Subject to any disclaimer, the term of this patent is extended or adjusted under 35 U.S.C. 154(b) by 785 days.

(21) Appl. No.: 12/525,975

(22) PCT Filed: Feb. 21, 2008

(86) PCT No.: PCT/GB2008/000608
§ 371 (c)(1),
(2), (4) Date: Jan. 5, 2010

(87) PCT Pub. No.: WO2008/102150
PCT Pub. Date: Aug. 28, 2008

(65) Prior Publication Data
US 2010/0119472 A1    May 13, 2010

(30) Foreign Application Priority Data

Feb. 21, 2007    (GB) .................................. 0703377.2

(51) Int. Cl.
| | |
|---|---|
| *A61F 13/00* | (2006.01) |
| *A61K 9/00* | (2006.01) |
| *A61K 9/06* | (2006.01) |
| *A61K 47/02* | (2006.01) |
| *A61K 47/18* | (2006.01) |
| *A61K 47/34* | (2006.01) |

(52) U.S. Cl.
CPC .............. *A61K 9/0043* (2013.01); *A61K 9/06* (2013.01); *A61K 47/02* (2013.01); *A61K 47/183* (2013.01); *A61K 47/34* (2013.01)

(58) Field of Classification Search
None
See application file for complete search history.

(56) References Cited

U.S. PATENT DOCUMENTS

| | | | | |
|---|---|---|---|---|
| 4,363,319 | A | | 12/1982 | Altshuler |
| 5,739,288 | A | * | 4/1998 | Edwardson et al. ........... 530/382 |
| 5,928,611 | A | * | 7/1999 | Leung ............................ 422/131 |
| 6,365,131 | B1 | | 4/2002 | Doshi et al. |
| 6,818,018 | B1 | * | 11/2004 | Sawhney ................... 623/11.11 |
| 7,544,348 | B2 | * | 6/2009 | Jacob et al. ....................... 424/49 |
| 2003/0077301 | A1 | | 4/2003 | Maibach et al. |
| 2005/0232868 | A1 | | 10/2005 | Rennie et al. |
| 2006/0115521 | A1 | | 6/2006 | Hudson et al. |
| 2007/0073210 | A1 | * | 3/2007 | Hille et al. ....................... 602/48 |

FOREIGN PATENT DOCUMENTS

| | | |
|---|---|---|
| EP | 0275054 A1 | 7/1988 |
| GB | 2081090 A | 2/1982 |
| GB | 2409162 A | 6/2005 |
| GB | 2447012 B | 3/2011 |
| WO | 9306855 A1 | 4/1993 |
| WO | 200100218 A1 | 1/2001 |
| WO | 03000155 A2 | 1/2003 |
| WO | WO 03000155 A2 * | 1/2003 |
| WO | 2006005340 A1 | 1/2006 |
| WO | 2008102150 A3 | 8/2008 |

OTHER PUBLICATIONS

Author Unknown, "Lubrizol Product Specification: Carbopol 971P NF Polymer," Lubrizol Advanced Materials, Inc., The Lubrizol Corporation, Edition: Sep. 9, 2011, Issue date: Jun. 14, 2007, 1 page.
Author Unknown, "Lubrizol Product Specification: Carbopol 974P NF Polymer," Lubrizol Advanced Materials, Inc., The Lubrizol Corporation, Edition: Sep. 9, 2011, Issue date: Jun. 14, 2007, 1 page.
Bende, Mats et al., "Effects of Glypressin on Human Nasal Mucosa," Acta Otolaryngol (Stockh) 1986, vol. 102, pp. 488-493.
Bende, Mats et al., "Topical Terlipressin (Glypressin®) Gel Reduces Nasal Mucosal Blood Flow but Leaves Ongoing Nose-bleeding Unaffected," Acta Otolaryngol (Stockh) 1990, vol. 110, pp. 124-127.
Bjelkengren, G., "Determination of a suitable dosage of lysine-vasopressin and triglycyl-lysine-vasopressin, given in a gel-solution locally in the rectum of rats for possible radioprotective purposes," Acta Oncologica, vol. 29, Fasc. 8, Apr. 23, 1990, pp. 1041-6.
Tibbelin, Anders et al., "Effect of Local Tranexamic Acid Gel in the Treatment of Epistaxis," S. Karger AG, Basel, Switzerland, vol. 57, 1995, pp. 207-209.
International Search Report and Written Opinion for International Patent Application No. PCT/GB2008/000608, mailed Mar. 16, 2009, 12 pages.
International Preliminary Report on Patentability for International Patent Application No. PCT/GB2008/000608, mailed Sep. 3, 2009, 9 pages.
Search Report for British Patent Application No. GB0703377.2, date of search Jun. 19, 2007, 2 pages.
Examination Report for British Patent Application No. GB0703377.2, mailed Sep. 29, 2010, 2 pages.

* cited by examiner

*Primary Examiner* — Susan Tran
(74) *Attorney, Agent, or Firm* — Withrow & Terranova, P.L.L.C.; Vincent K. Gustafson

(57) ABSTRACT

The invention relates to a gel composition comprising: a) a carboxy polymethylene polymer; b) glycine; c) a source of calcium ions; and d) water. The invention also extends to a dry composition comprising the aforementioned components a), b) and c). The gel compositions of the invention are useful for the prophylaxis and treatment of epistaxis. The gel compositions can be easily administered to the nasal cavity and do not require removal after use.

14 Claims, No Drawings

COMPOSITION FOR COMBATING EPISTAXIS

CROSS-REFERENCE TO RELATED APPLICATIONS

This application is a U.S. national phase under the provisions of 35 U.S.C. §371 of International Application No. PCT/GB08/00608 filed on Feb. 21, 2008, which in turn claims priority of Great Britain Patent Application No. 0703377.2 filed on Feb. 21, 2007. The disclosures of such international application and Great Britain priority application are hereby incorporated by reference herein in their respective entireties, for all purposes.

The present invention relates to a novel composition that is useful in the treatment of epistaxis (nosebleeding). In particular, the invention relates to a gel composition for the prophylaxis and treatment of epistaxis that can be easily administered to the nasal cavity and does not require removal after use.

BACKGROUND OF THE INVENTION

Epistaxis (nosebleed) is very common. Although in most cases the symptoms are temporary and non-recurrent, some patients experience recurring and severe symptoms. The most common method of treating severe epistaxis is by cauterization of the bleeding vessel. When the source of bleeding cannot be seen, intranasal packing using cotton tampons or inflatable rubber balloons may be employed, but such methods cause inconvenience and discomfort for the patient. The cotton tampons typically have a width of 2 cm and a length of 40-100 cm. They are pressed into the nose to stop bleeding by applying pressure to the nasal mucosa and may stay in place for 1-4 days. Inflatable rubber balloons also act by applying pressure to the nasal mucosa, and may remain in place for 1-2 days. Whether tampons or balloons are employed, either is painful when inserted, interferes with normal breathing and may lead to local infection. There is a need for treatments which do not have such disadvantages.

WO 01/00218 describes a nasal spray formulation which includes Dead Sea salt in a concentration of about 0.5 to 5 g/l of sterile aqueous solution, contains a buffer and is essentially free of noxious, organic impurities. The formulation is said to be for use in treating rhinitis, sinusitis, epistaxis and post-surgical irritation, but no trials relating to epistaxis are reported.

Different nasal gel applications and vasoconstrictors have been studied experimentally, see Bende et al, *Acta Otolaryngol (Stockh)* 88, 459-461 (1979); Bende et al, *Acta Otolaryngol (Stockh)* 102, 488-493 (1986); and Bende et al, *Acta Otolaryngol (Stockh)* 110, 124-127 (1990). Earlier clinical investigations indicated that fibrinolysis plays a role in recurrent epistaxis, see Petruson et al, *Acta Otolaryngol (Stockh)* suppl. 317 (1974). Tibbelin et al, *ORL (Basel)* 57, 207-209 (1995) explored the haemostatic effect of local application of a tranexamic acid gel and a placebo gel in a randomized, double-blind, multicentre clinical trial. Both gels were found to have a beneficial effect, and surprisingly the placebo gel was found to be slightly (though not significantly) better than that containing the tranexamic acid (an inhibitor of the fibrinolytic system).

SUMMARY OF THE INVENTION

The inventor has surprisingly discovered an improved composition for use as a nasal gel, which composition has all the advantageous properties of the aforementioned known placebo gel, whilst being more effective in the treatment of epistaxis.

According to the invention there is provided a gel composition comprising:
 (a) a carboxy polymethylene polymer;
 (b) glycine;
 (c) a source of calcium ions; and
 (d) water.

Additional materials may also be used that are conventional in the art of formulating such compositions, as discussed in more detail below.

The invention also provides a process for making the novel gel composition, comprising mixing water with the dry components (a), (b) and (c) above, in any desired order.

In a further aspect, the invention provides a method of treatment of epistaxis by prophylaxis or therapy, comprising inserting into a nasal cavity of a human or non-human animal an effective amount of a gel composition of the invention.

In a yet further aspect, the invention provides a gel composition of the invention for use in therapy, especially for use in the treatment of epistaxis.

In a still further aspect, the invention provides the use of a gel composition of the invention in the treatment of epistaxis by prophylaxis or therapy.

Although the compositions are used for therapy in the form of gels, it is also possible to prepare compositions of the dry ingredients (a), (b) and (c) above, and then prepare gel compositions at a subsequent time, prior to use. Accordingly, in a still further aspect, the present invention provides a dry composition comprising:
 a) a carboxy polymethylene polymer;
 b) glycine; and
 c) a source of calcium ions.

DETAILED DESCRIPTION OF THE INVENTION

The nature and role of the essential components of the compositions of the invention are now described in more detail.

a) Carboxy Polymethylene Polymer

Carboxy polymethylene polymers (also known as carbomers) are polymers of acrylic acid cross-linked with polyalkenyl ethers or divinyl glycol. Carbomers have the basic structural unit $-[CH_2CH(COOH)-]_n$. They are available in a range of grades from Noveon, Cleveland, Ohio, USA, under the brand name CARBOPOL® (a registered trademark of Lubrizol Advanced Materials, Inc., Cleveland, Ohio, USA). The grades differ according to the degree of cross-linking and manufacturing conditions. Raw carbomer polymers are white powders, but they are strongly hydrophilic, being capable of swelling in water up to 1000 times their original volume to form a gel. Carbomers are essentially biologically inert and have a long history of safe use in topical formulations of various kinds. They are known to adhere to mucosal surfaces as they attract water from the mucosal layer adherent to the epithelial surface.

When introduced into the nasal cavity the carbomer has the effect of exerting a pressure on the mucosa and the bleeding vessel. In this way it acts like a tampon, which also exerts pressure against the mucosa and is used as treatment for epistaxis (see Background section above). However, the gel has the advantage over the tampon that there is usually no need to remove it, since it is transported by the mucociliary system through the nose backwards to the throat and is then swallowed within an hour or two after administration.

Preferred carboxy polymethylene polymers for use in the present invention are those sold under the trade name CARBOPOL®, available from Noveon. CARBOPOL® 974P NF and CARBOPOL® 971 P NF are particularly preferred polymers.

The amount of carboxy polymethylene polymer used will vary depending on the identity of the polymer(s). The carboxy polymethylene polymer typically constitutes from 5 to 50% by weight of the total dry ingredients, preferably from 10 to 35 wt. %, more preferably from 15 to 30 wt. %, most preferably about 20 wt. %.

Gel compositions of the invention can be formed using a concentration of carboxy polymethylene polymer which is typically from 10 to 100 g dry weight per liter of gel, preferably from 20 to 50 g/l, more preferably from 30 to 40 g/l, most preferably about 35 g/l.

b) Glycine

The second component in the gel is the amino acid glycine (aminoacetic acid). It is not a so-called "essential amino acid", and can be produced by the human body itself being the simplest of all the 20 amino acids. Glycine is involved in a great variety of metabolic reactions and takes part in the formation of proteins in the human body.

We have found that glycine confers a hyperosmotic activity on the gel. Water is drawn from the nasal mucosa, which means that the mucosa becomes decongested and shrinks, the blood-flow into the vessels decreases and the bleeding may be arrested. As glycine is a building-block for human cells it may also play a rôle in the restoration of the nasal mucosa and blood vessel wall.

Glycine is a widely commercially available material.

In the dry compositions of the invention glycine typically constitutes from 30 to 90% by weight of the total ingredients, preferably from 50 to 80 wt. %, more preferably around 70 wt. %.

In the gel compositions of the invention, the concentration of glycine is typically from 50 to 200 g dry weight per liter of gel, preferably from 80 to 150 g/l, more preferably from 110 to 120 g/l, most preferably about 117 g/l.

c) Source of Calcium Ions

The third essential component is a source of calcium ions ($Ca^{2+}$). Calcium ions are implicated in biological coagulation processes. In the last steps of blood coagulation thrombin transforms the protein fibrinogen (molecular weight 340,000) to soluble fibrin. Finally, the soluble fibrin can be converted to an insoluble fibrin, which can withstand mechanical forces much more effectively, as a result of which a rebleeding may be prevented. Without wishing to be bound by any theory, it is believed that the conversion of fibrin to an insoluble form proceeds more rapidly in the presence of calcium ions, the absorption of which may be enhanced as a result of the nasal mucosa being very thin.

The calcium ions may be present in any convenient form, but are preferably in the form of a soluble salt, for example the chloride, or another salt, e.g. acetate, phosphate, carbonate or gluconate. Calcium chloride is most preferred.

The total amount of calcium ions is typically from 0.005 to 0.1% by weight of the total dry ingredients, preferably from 0.01 to 0.05 wt. %, more preferably from 0.025 to 0.040 wt. %, most preferably about 0.035 wt. %, expressed as the weight of $Ca^{2+}$ ions only, based on the total weight of dry ingredients.

In the gel compositions of the invention, the concentration of calcium ions is typically from 10 to 200 mg per liter of gel, preferably from 20 to 100 mg/l, more preferably from 40 to 70 mg/l, most preferably about 58 mg/l.

Other Components

Water is employed when formulating the compositions in the form of a gel, e.g. prior to administration to the patient. The amount of water used is that required to form a gel of the appropriate viscosity when mixed with the other components. This will vary depending on the identity of the carboxy polymethylene polymer(s) used. Typically, water comprises 750-950 g per kg of gel, preferably 800-900 g/kg, more preferably around 850 g/kg.

In addition to the three essential components discussed above, other additional materials may also be used that are conventional in the art of formulating such compositions, for example pH adjusting agents (acids, alkalis, buffers), preservatives (e.g. methargen, propagin), antioxidants, pigments and dyes, fragrance materials, excipients, carriers and the like.

Process Conditions

In order to formulate the compositions of the invention as gels for clinical use, the following steps are carried out.

A source of calcium ions, e.g. calcium chloride, is dissolved in water. Before or after mixing with the source of calcium ions, a suitable amount of acid, alkali or buffer material may be added to the water in order to ensure that the final gel has a suitable pH, e.g. in the range 6.5-7.5. Glycine is then added with stirring until dissolution is complete. Carboxy polymethylene polymer is then added slowly and carefully (e.g. by gradually sprinkling the powder into the aqueous liquid) with stirring. Stirring is continued until all the polymer has dissolved. The pH of the gel may be checked to ensure that it is within the required range of 6.5-7.5.

The order in which the components of the gel are combined may be varied from that described in the foregoing paragraph. For example, the dry ingredients may firstly be mixed together, and then water is added in a suitable quantity to form a gel of appropriate viscosity. For any given combination of dry ingredients, the skilled person can establish, e.g. by trial and error, the amount of water that is suitable for forming a gel of appropriate viscosity.

The preparation of the gel may be carried out at any suitable temperature. However, preparation at room temperature is most convenient.

The conditions of the foregoing process can be varied and optimised in a manner familiar to a person skilled in the art.

Manner of Administration

The compositions are used in the form of gels. Prior to use, the patient should be asked to blow his nose. Preferably the internal nasal surfaces should then be gently cleansed, in order to maximise contact between the gel and the nasal mucosa. Next, the gel should be inserted in the nostril(s) that are subject to bleeding, for example using a prefilled syringe. Preferably the entire nasal cavity should be filled. (This can be done by discontinuing the administration of the gel when the patient indicates that the gel is beginning to run down the back of the nasal cavity into his throat.) However, it may not be necessary to fill the entire nasal cavity if the bleeding has clearly ceased before filling is complete. A small piece of cotton or other suitable plug may then be placed in the patient's nostril. The patient should refrain from blowing his nose for a sufficient time to allow the gel to be effective, for example 30 minutes.

EXAMPLE

The following Example of the manufacture and use of the invention is provided in order to illustrate the invention only, and are not to be taken as limiting its scope.

504 g Pure water and 352 ml (366 g) of 1M sodium hydroxide solution were placed together in a glass vessel. 185 mg of calcium chloride ($CaCl_2.2H_2O$) was added and the mixture was stirred until the calcium chloride had dissolved. 100 g Glycine was then added with stirring until dissolution was complete. 15 g of CARBOPOL® PNF 974 and 15 g of CARBOPOL® PNF 971 were added with stirring. The velocity of stirring was increased continuously as the resulting gel became ever more viscous. Stirring was continued until all the carbomer had dissolved. All the foregoing steps were carried out at room temperature. The gel was checked to ensure that its pH was within the required range of 6.5-7.5.

The invention claimed is:

1. A gel composition for intranasal application, the composition comprising:
   a) a carboxy polymethylene polymer at a concentration of from 20 to 50 grams dry weight per liter of gel;
   b) glycine at a concentration of 50 to 200 grams dry weight per liter of gel;
   c) a source of calcium ions, wherein the concentration of calcium ions is from 20 to 100 milligrams per liter of gel; and
   d) water.

2. The gel composition of claim 1 wherein the concentration of carboxy polymethylene polymer is about 35 g dry weight per liter of gel.

3. The gel composition of claim 1 wherein the concentration of glycine is about 117 g dry weight per liter of gel.

4. The gel composition of claim 1 wherein the concentration of calcium ions is about 58 mg per liter of gel.

5. A process for making the gel composition of claim 1, comprising mixing water with components (a), (b), and (c) in dry form, in any desired order.

6. A method of prophylaxis or therapy of epistaxis, comprising inserting into a nasal cavity of a human or non-human animal an effective amount of the gel composition of claim 1.

7. A medicament for prophylaxis or therapy of epistaxis, the medicament comprising the gel composition of claim 1.

8. A method of manufacturing a gel composition according to claim 1 for prophylaxis or therapy of epistaxis, the method comprising the step of combining a dry composition comprising (a) a carboxy polymethylene polymer, (b) glycine, and (c) a source of calcium ions, with a water-containing liquid.

9. The method of claim 8, wherein the liquid consists of water.

10. The gel composition of claim 1 wherein the concentration of carboxy polymethylene polymer is about 35 grams dry weight per liter of gel; the concentration of glycine is about 117 grams dry weight per liter of gel; and the concentration of calcium ions is about 58 milligrams per liter of gel.

11. The gel composition of claim 1 wherein the concentration of carboxy polymethylene polymer is in a range of from 30 to 40 grams dry weight per liter of gel.

12. The gel composition of claim 1 wherein the concentration of glycine is in a range of from 110 to 120 grams dry weight per liter of gel.

13. The gel composition of claim 1 wherein the concentration of calcium ions is in a range of from 40 to 70 grams dry weight per liter of gel.

14. The gel composition of claim 1 wherein the concentration of carboxy polymethylene polymer is in a range of from 30 to 40 grams dry weight per liter of gel, the concentration of glycine is in a range of from 110 to 120 grams dry weight per liter of gel, and the concentration of calcium ions is in a range of from 40 to 70 grams dry weight per liter of gel.

* * * * *